(12) United States Patent
Genovese et al.

(10) Patent No.: US 8,161,797 B1
(45) Date of Patent: Apr. 24, 2012

(54) SAMPLING DEVICE FOR LOW VOLATILITY HAZARDOUS CHEMICALS

(75) Inventors: James A. Genovese, Street, MD (US); Edward M. Rychwalski, Abingdon, MD (US); Stephen J. Comaty, Belcamp, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 359 days.

(21) Appl. No.: 12/687,191

(22) Filed: Jan. 14, 2010

(51) Int. Cl.
*G01N 1/22* (2006.01)
(52) U.S. Cl. ............... 73/31.03; 73/31.01; 73/31.02; 73/863.11; 73/863.21; 73/864.81
(58) Field of Classification Search ........ 73/23.3–23.35, 73/24.01, 31.01–31.03, 31.07, 863, 863.11, 73/863.21, 864.81
See application file for complete search history.

(56) References Cited

U.S. PATENT DOCUMENTS

| | | | |
|---|---|---|---|
| 2005/0276727 A1* | 12/2005 | Pawliszyn et al. | 422/99 |
| 2006/0094922 A1* | 5/2006 | Hunt et al. | 588/304 |
| 2008/0241000 A1* | 10/2008 | Jung et al. | 422/100 |
| 2009/0151459 A1* | 6/2009 | Donaty | 73/662 |
| 2009/0227005 A1* | 9/2009 | Jung et al. | 435/287.2 |
| 2010/0301199 A1* | 12/2010 | Chen et al. | 250/282 |

* cited by examiner

*Primary Examiner* — David Rogers
(74) *Attorney, Agent, or Firm* — Ulysses John Biffoni

(57) ABSTRACT

A device for use with a detection means and a solvent source for sampling low volatility hazardous chemicals within a sample matrix is comprised of a sonicator having a probe for providing mechanical agitation to the sample matrix; means for transporting solvent gas from the solvent source to the sample matrix; means for transporting sample gas from the sample matrix to the detection means; and a heating element for heating the sample gas, solvent gas, and sample matrix. The device may include a thermocouple for providing a temperature reading. It also may include a plurality of interchangeable probe tips of different shapes.

16 Claims, 4 Drawing Sheets

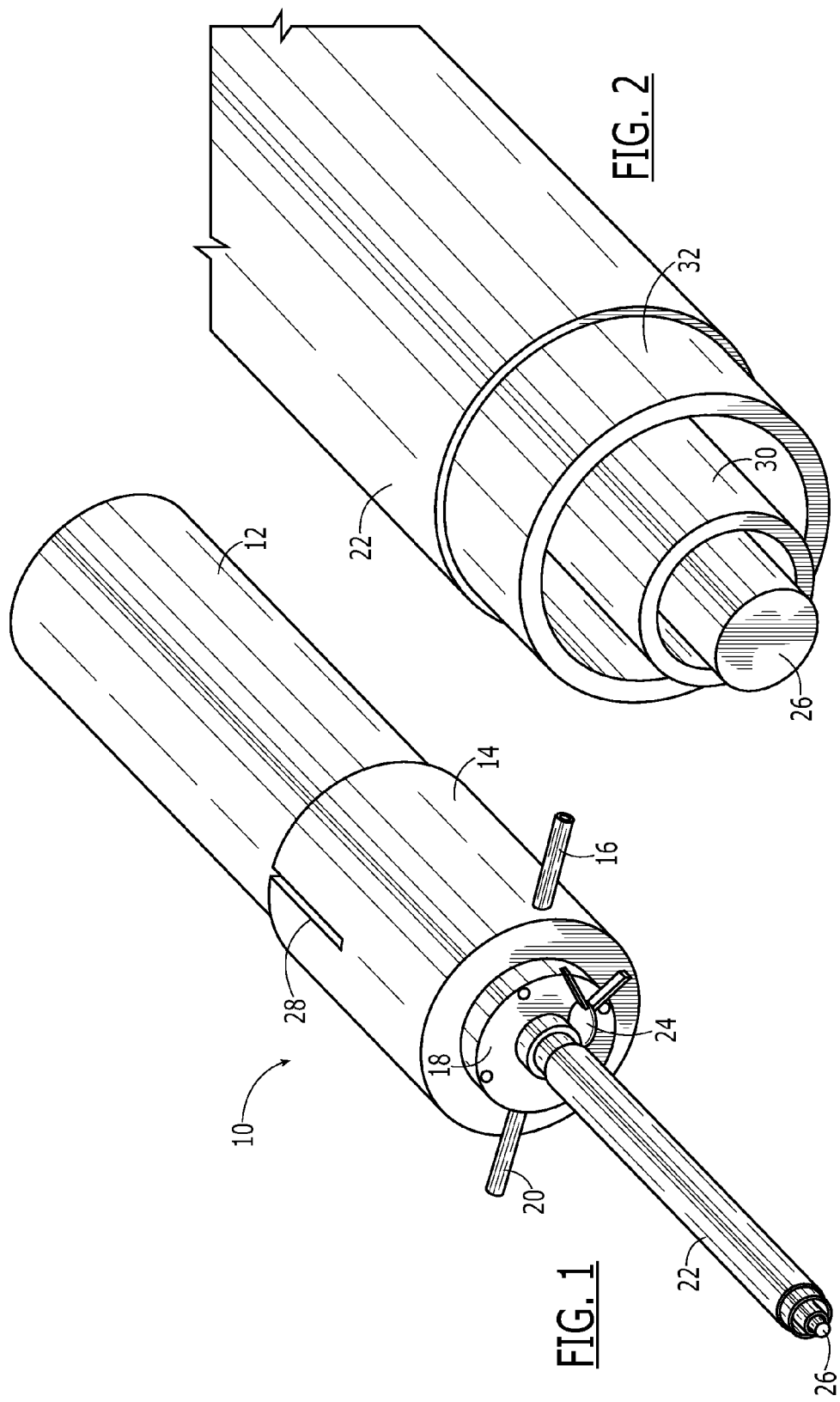

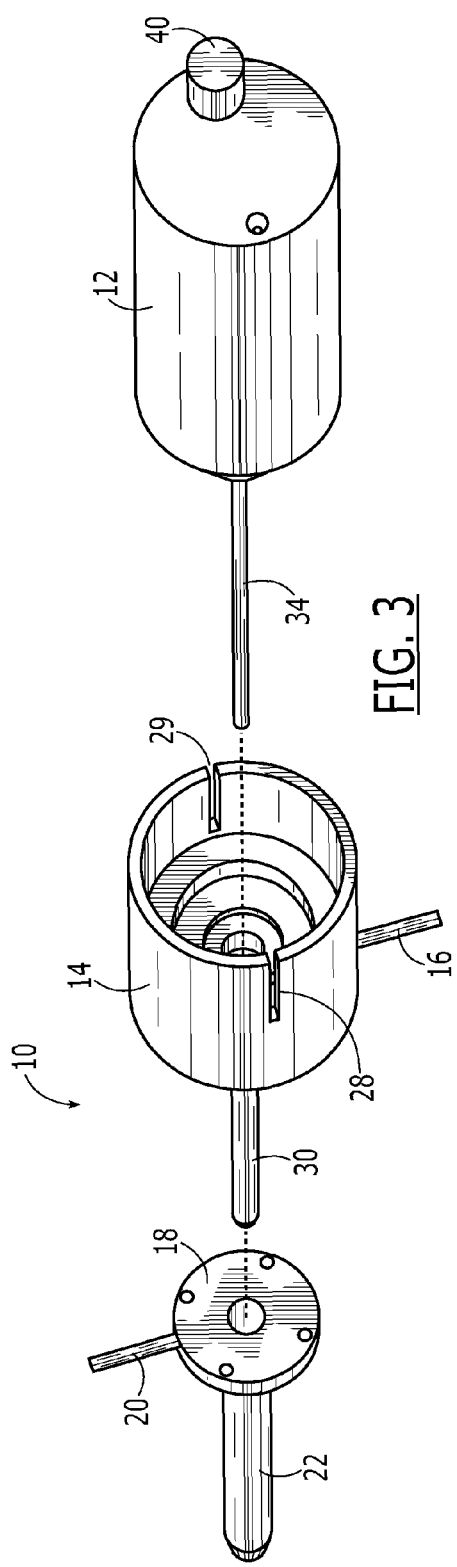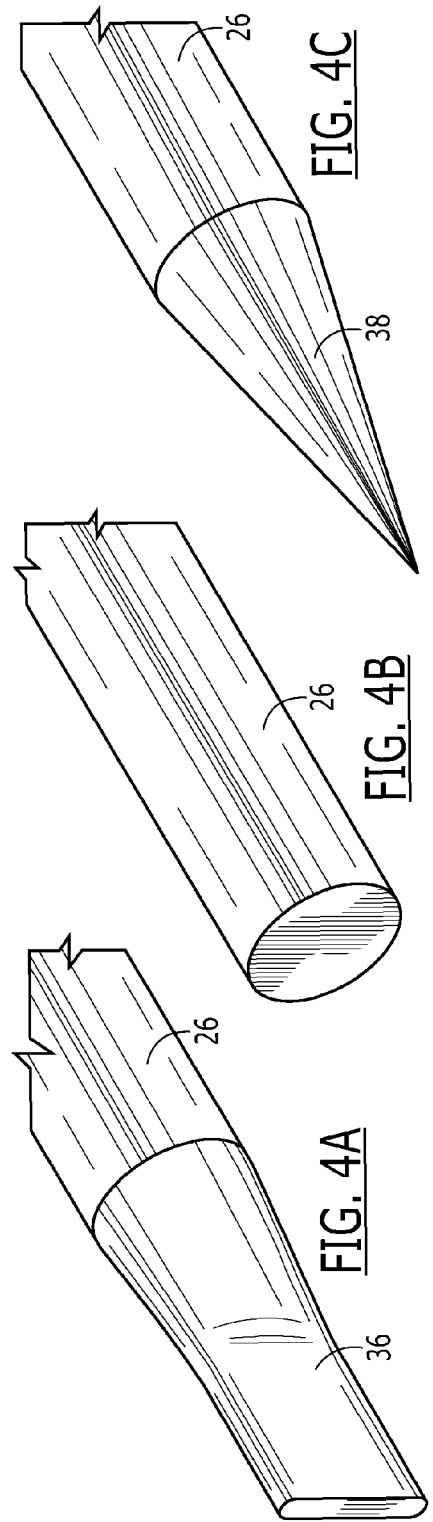

SAMPLING DEVICE FOR LOW VOLATILITY HAZARDOUS CHEMICALS

GOVERNMENTAL INTEREST

The invention described herein may be manufactured, used and licensed by or for the U.S. Government.

TECHNICAL FIELD

This invention relates to the sampling and detection of low volatility hazardous chemicals.

BACKGROUND

At present, a number of handheld detectors are available for use in detecting hazardous vapors. These are used by fire fighters, hazmat teams, and others to detect the presence of toxic industrial chemicals, explosive or flammable gases, and chemical warfare agents. Examples of handheld detectors relevant to the present invention include but are not limited to products sold under the trademarks AP4C (Proengin of France), MINIRAE (RAE Systems, Inc.), HGVI and LCD 3.2e (both of Smiths Detection, Inc.).

One limitation of such devices is that an adequate concentration of the analyte or chemical compound to be detected must be available to the sensor element of the detector. This can pose a problem with low volatility hazards, such as certain chemical warfare agents. By way of example, the nerve agent referred to as VX is a sulfonated organophosphorous compound that is highly lethal. VX, however, has a very low vapor pressure in the operational temperature ranges in which it must be detected. For example, at 25 degrees Celsius (° C.), VX has a vapor pressure of only 0.00063 millimeters of Mercury (mm Hg). In comparison, the vapor pressure of water at the same temperature is 23.8 mm Hg, which is roughly 38,000 times that of VX. With such a low vapor pressure, VX is difficult to detect with devices such as the detectors mentioned above. Samples taken for subsequent laboratory analysis suffer from the same problem. Accordingly, what is needed is a low volatility hazard sampling device that when used with the available detection devices or laboratory instruments will provide an accurate and dependable determination of the presence of agent in the sample matrix even when such agent is of the low-volatility type.

SUMMARY

A device for use with a detection means and a solvent source for sampling low volatility hazardous chemicals within a sample matrix is comprised of a sonicator having a probe for providing mechanical agitation to the sample matrix; means for transporting solvent gas from the solvent source to the sample matrix; means for transporting sample gas from the sample matrix to the detection means; and a heating element for heating the sample gas, solvent gas, and sample matrix. The device may include a thermocouple for providing a temperature reading. It also may include a plurality of interchangeable probe tips of different shapes.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1 is a perspective view of a low volatility hazard sampling device according to an embodiment of the present invention.

FIG. 2 is a perspective view of the probe tip area of the embodiment shown in FIG. 1.

FIG. 3 is an exploded view of the embodiment shown in FIG. 1.

FIGS. 4A-4C provide a perspective view of three sonicator probe tip embodiments as taught for use with the present invention.

DETAILED DESCRIPTION

Figure 5:
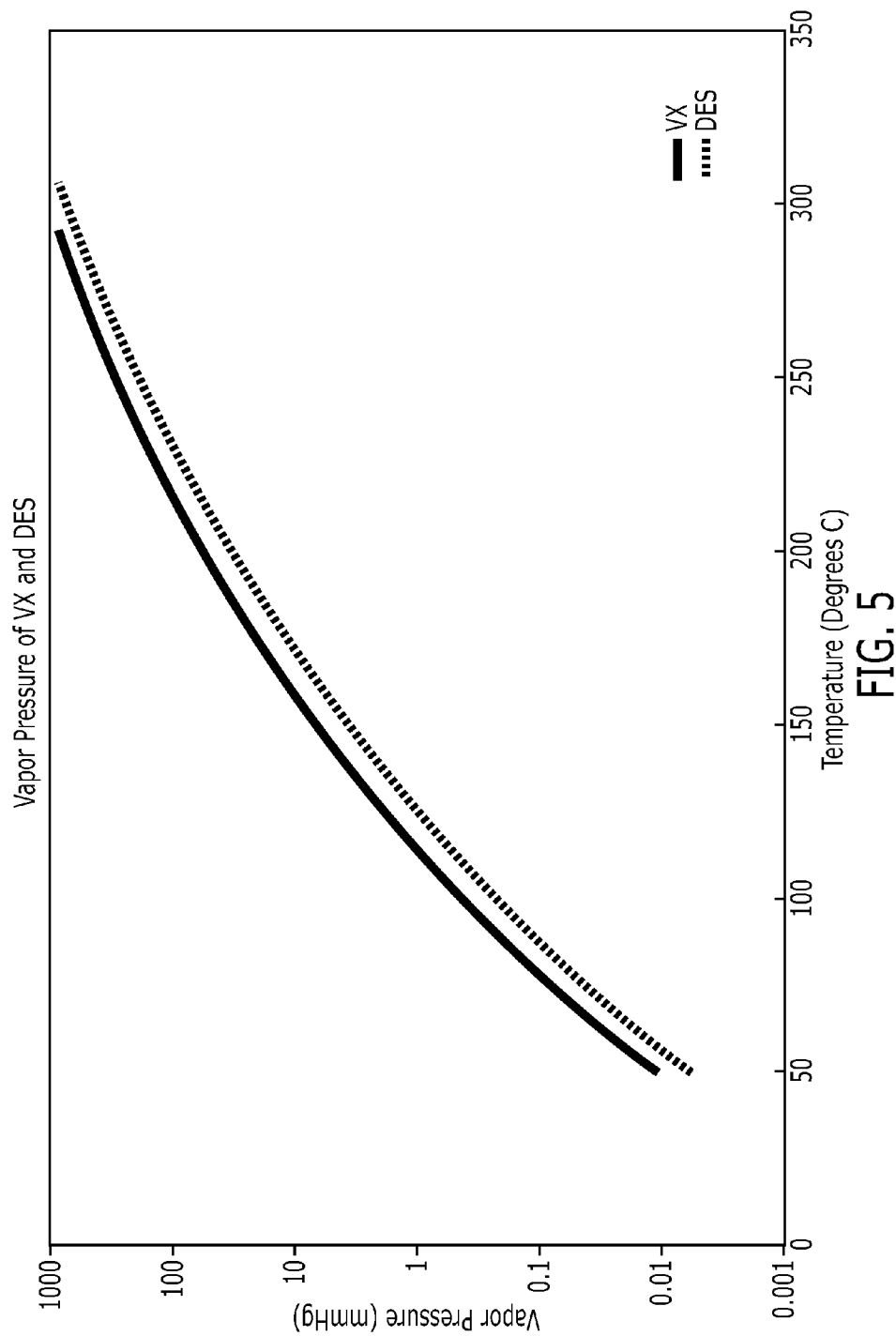
FIG. 5 is a graph of the vapor pressure of VX and DES in mm Hg for temperatures from 50 to 300° C.

A device 10 for sampling low volatility hazardous materials for use with handheld detectors or other instruments is shown in FIG. 1. As will be apparent from the following description, device 10 can be used with a number of handheld detectors, including but not limited to those sold under the trademarks AP4C (Proengin of France), MINIRAE (RAE Systems, Inc.), and HGVI and LCD 3.2e (both of Smiths Detection, Inc.). The present invention also can be used with larger, laboratory-type analytical instruments, including but not limited to a gas chromatograph (GC), mass spectrometer (MS), or a combination of such instruments. In addition, device 10 can be used as a sample collection device independent of any particular detector or analytical instrument. Accordingly, the term "detection means" is used herein to refer to all of these options for handling and analyzing the sample gas.

Sonicator 12 in this embodiment is a handheld ultrasonic device having an elongated ultrasonic probe tip 26 for providing mechanical agitation to a sample matrix. Various sonicators for use as a component of the present invention are available commercially and can be selected from a number of sources and models. Preferably, sonicator 12 is compact, lightweight, and fit for use in an outdoor environment where it may be exposed to a wide range of weather conditions. Probe tip 26, as well as the body of the probe, is preferably made of material such as titanium or stainless steel so as to provide effective transmission of ultrasonic energy as well as corrosion resistance. The tip energy of the sonicator should be sufficient to provide effective mechanical agitation in a number of sample matrices when placed in contact or close proximity to the sample matrix. The term "sample matrix" as used herein refers to the material containing the analyte from which the sample is taken with the present invention. As such, the sample matrix could be a solid surface such as a tile floor or a hard wall surface material, a loose solid such as soil, a flexible material such as carpet, a gas such as the air within a room or a piece of equipment such as a computer, or in the form of a liquid including but not limited to water.

Sonicators usable in accordance with the present invention include, by way of example, the device sold under the trademark SONOZAP by BioSpec Products, Inc., which is an ultrasonic homogenizer with a titanium probe of ⅛-inch diameter and six-inch length with stated tip energy of 125 Watts/cm$^2$ and a 90-micron stroke. In addition, the stroke speed of the SONOZAP device is adjustable by way of a control knob located on the far end of sonicator 12 as viewed in FIG. 1 (said control knob visible in FIG. 3).

As illustrated in FIG. 1, a first manifold 14 provides a housing for sonicator 12 and a means for flowing solvent gas from inlet port 16 to the area near probe tip 26, as will be explained in detail in reference to FIGS. 2-3. Manifold 14, including inlet port 16, is preferably made of corrosion resistant, non-reactive material that is suitable for outdoor exposure and that will not adsorb solvent or sample gas. In the embodiment illustrated here, manifold 14 includes one or more expansion slots 28 for a compression-type fitting with sonicator 12.

A second manifold 18 is attached to first manifold 14 and provides a means for flowing sample gas from the sample matrix in proximity to probe tip 26 to outlet port 20 where the sample gas can flow directly to the detection means, which as noted above may be a handheld detector, laboratory-type instrument, or a storage vessel (none of which are shown) for subsequent analysis. A solvent source (not shown) is attached to inlet port 16 using flexible tubing or the like. Similarly, the detector, instrument, or storage vessel is connected to outlet port 20 using flexible tubing or the like. Such flexible tubing, if used, should be a heatable type so as to allow for the application of heat to reduce condensation in the tubing. In alternative embodiments, a handheld detector, or solvent source, or both could be fixed relative to the device of the present invention so that some or all of the tubing is rigid. These tubes, whether flexible or rigid, may be equipped with one or more thermocouples and may be electronically temperature controlled. Further details of gas flow are described below in reference to FIGS. 2-3.

Manifolds 14 and 18 are preferably made of the same or compatible materials that are suitable for heating through convection from a heating element, inert so as not to react with the solvent or sample gas, and corrosion resistant. One such suitable material is stainless steel. The same, or a compatible material, can be used for inlet port 16, outlet port 20, and conduits 30, 32 (the latter is shown in FIG. 2). These components, for example, may be fabricated from stainless steel tubing and fastened to manifolds 14, 18 through well-known means such as welding, threaded fittings, or compression fittings.

Heating element 22, as illustrated in the embodiment of FIG. 1, is a flexible heating wrap that is placed around and secured in contact with outlet conduit 32 (shown in FIG. 2). When activated, heating element 22 heats conduit 32, thereby heating the gas flowing through both the outlet conduit 32 and inlet conduit 30. In this way, the solvent gas, sample matrix, and sample or outlet gas are all heated above ambient conditions. A number of commercially available heaters are suitable for use as heating element 22. By way of example, the heater sold under the trademark KAPTON by Watlow, Inc., is a suitable commercially available product for heating source 22 as it is easily applied to the contour of conduit 32 (shown in FIG. 2), will not effect sampling results by off-gassing, and the surface is easily cleaned with most cleaning materials. Alternatively, other types of heaters may be used in place of heating element 22. In addition, an infrared heater could be mounted on device 10 anywhere that it is convenient to do so. If used, the infrared heater would be directed or pointed at the sample matrix so that the infrared energy is delivered to the sample matrix causing it to heat.

As illustrated in FIG. 1, thermocouple 24 may be included as a component of the present invention to provide a temperature reading to ensure that heating element 22 is performing as intended. Additional thermocouples could be used for other heated components, such as mounted on the heated tubing from outlet port 20 to the detector. Thermocouple 24 can be attached to manifold 18 or conduit 32 (shown in FIG. 2) using standard attachment means such as an adhesive made for high-temperature applications. Thermocouple 24 is not, however, required for the present invention to function as sampling performance is not effected or controlled by the thermocouple 24 and the heat from heating element 22 will be readily apparent to the user when device 10 is in operation. Thermocouple 24 can be used for quality control where an approved protocol calls for a temperature reading within a specified range for consistency of detection results. When a thermocouple 24 is used, an electrical lead (not shown) is attached to thermocouple 24 on one end and to a readout meter (not shown) on the other end.

Turning to FIG. 2, a perspective view of the probe tip area is provided. As shown here, probe tip 26 protrudes from inlet conduit 30, which in turn protrudes from outlet conduit 32. Heating element 22, a flexible heating wrap as illustrated in this embodiment, is wrapped around and secured in contact with outlet conduit 32. The diameters of probe tip 26, inlet conduit 30, and outlet conduit 32 may vary from one embodiment to another while still performing the functions as taught herein. Similarly, the amount of protrusion between these components, as well as the shape of probe tip 26, may vary from one embodiment to another while still performing the functions as taught herein. The functions are as follows. The end of probe tip 26 is exposed to the sample matrix so as to allow the probe to impart mechanical agitation of the sample matrix. A first flow space for solvent gas is provided between the probe body and the inner wall of inlet conduit 30. A second, and separate, flow space is provided between the outer wall of inlet conduit 30 and the inner wall of outlet conduit 32. In addition to the other variations mentioned here, the relative positions of the inlet and outlet conduits can be reversed, although the position described above reflects the preferred embodiment. That is, the first flow space described above could be used for the sample gas instead of the solvent gas with the second flow space used for the solvent gas. Similarly, while a circular cross-section as shown represents the preferred embodiment, other cross-sectional shapes are possible. Additionally, while the location of the probe 26 within inlet conduit 30, and inlet conduit 30 within outlet conduit 32 represents the preferred embodiment, it is possible to perform this function with alternative structure such as parallel conduits. The parallel conduits could terminate near probe tip 26 or could be joined into a probe manifold.

Turing to FIG. 3, an exploded view of the embodiment shown in FIG. 1 is provided to illustrate additional features. The three main parts of device 10 are sonicator 12 and manifolds 14, 18. Control knob 40 of sonicator 12 is visible in this view. Probe body 34 also is visible in this view as is the sonicator housing formed by the interior of manifold 14. Manifold 14 includes inlet port 16, expansion slots 28-29, and inlet conduit 30. Expansion slots 28-29 provide flexibility of manifold 14 for a compression fitting with sonicator 12. That is, sonicator 12 can be mounted within manifold 14 by simply pressing it into the interior of manifold 14. Alternative embodiments may use other attachment means including threaded fittings, however the preferred embodiment as shown here does not require any modification to sonicator 12. Inlet port 16 is confluent with inlet conduit 30. That is, gas or liquid can flow freely between inlet port 16 and inlet conduit 30. When sonicator 12 is placed within the housing formed by manifold 14 it seals off the opening of the housing so that any gas within the manifold, including that within inlet port 16 and inlet conduit 30, cannot escape out of the housing-sonicator junction.

Second manifold 18 includes outlet port 20 and outlet conduit 32, the latter not visible in FIG. 3 as heating element 22 is covering it. Outlet port 20 and outlet conduit 32 are confluent, allowing gas or liquid to flow freely between them. Manifold 18 is attached to manifold 14 by means of screws, bolts, threads, or the like. It could also be welded to or otherwise fixed permanently to manifold 14 by an appropriate adhesive made for high-temperature applications. As shown here, to assemble device 10, probe body 34 is inserted into manifold 14 and its inlet conduit 30, which in turn, is inserted into manifold 18 and its outlet conduit 32 (the latter shown in FIG. 2).

Turning to FIG. 4, a perspective view of three sonicator probe tip embodiments as taught for use with the present invention is provided. Probe tip 26 represents the flat-end configuration as illustrated in the previous figures. Alternative probe tip shapes 36, 38 are provided by way of illustration of shapes that could be used to apply mechanical agitation in small spaces such as corners formed by the intersection of floor and wall surfaces, small spaces within equipment such as computers, various cracks or cavities, and the like. These alternative probe tips 36, 38, as well as other probe tip shapes, can be attached to the probe body by way of threaded fastener, compression fitting, bayonet-type connection, or the like. While the preferred embodiment allows for the interchangeability of probe tips using one of these types of attachment means, the probe tip could be fastened to the probe body using an adhesive made for high-temperature applications. Alternatively, a set of probes having different tips could be used.

Having described and illustrated the various structural elements of the present invention, attention is now turned to the results in detection capability provided by sonic agitation when attempting to detect a low-volatility analyte in a sample matrix. In the graph of FIG. 5, the vapor pressure of VX and diethyl sebacate (DES) in mm Hg for temperatures from 50 to 300 degrees Celsius is provided to illustrate the similarity of VX and DES in their low volatility properties. DES, like VX, is not easily detected at typical room and outdoor temperatures because of this low volatility. Unlike VX, it is not a highly toxic chemical and therefore was selected as a surrogate for VX in an experiment to illustrate the effects of sonic agitation of the sample matrix on detector performance.

The detector used in this illustration is an ion mobility spectrometry (IMS) type detector sold under the trademark LCD 3.2E. The type of detector is capable of detecting and identifying very low concentrations of chemicals based upon the differential migration or drift time of gas phase ions across an electric field. To perform the experiment, the LCD 3.2E was placed at a fixed height over an ultrasonic bath. The LCD 3.2E was configured to allow data logging using software sold under the trademark TRIMSCAN, which was installed on a laptop.

Figure 6:
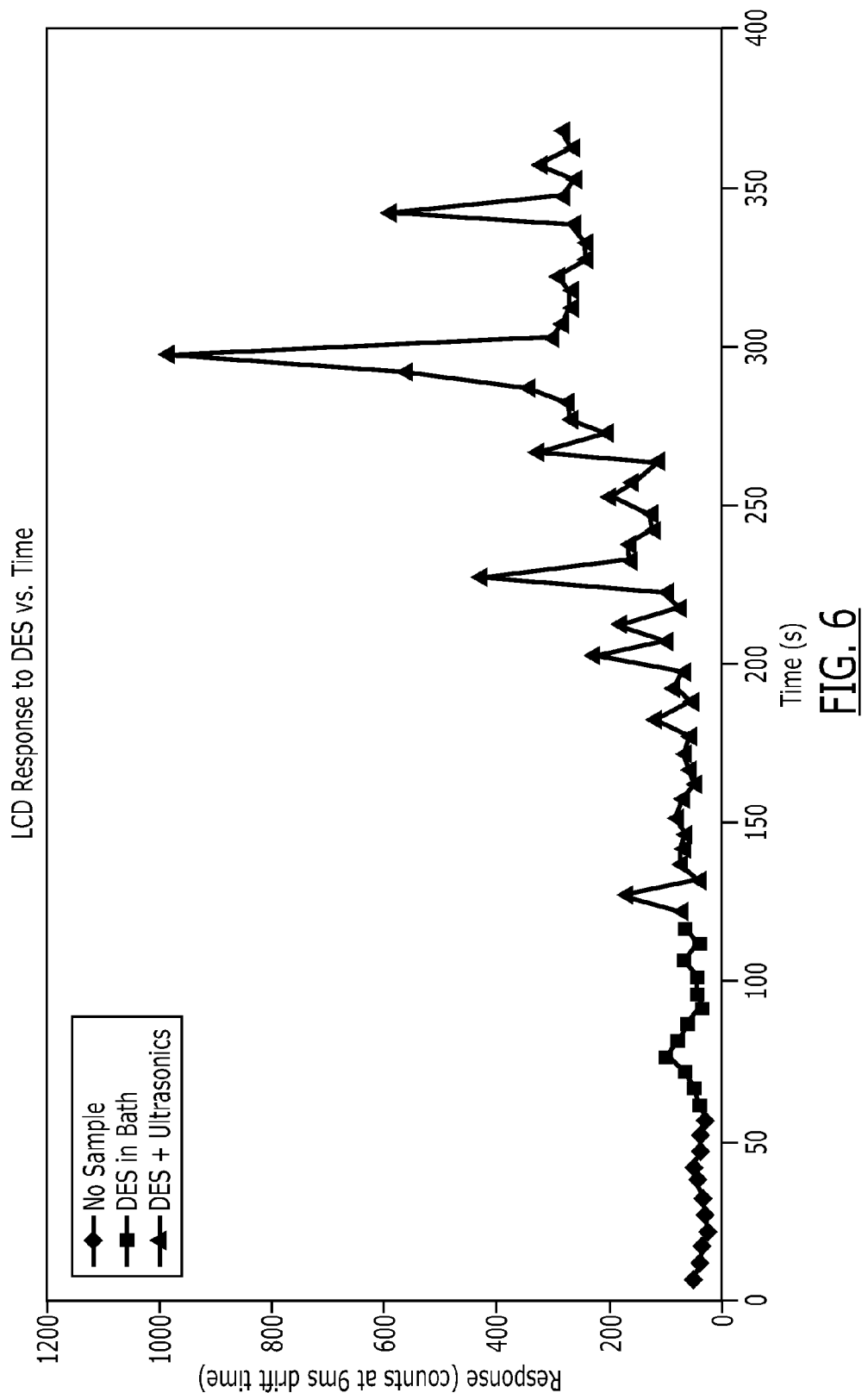
FIG. 6 is a graph of detector response to DES over time illustrating changes that occur in detector readings when DES is added and when ultrasonic mechanical agitation is added, respectively.

FIG. 6 is a graph of the data collected. The LCD 3.2E was powered up and a baseline was established for the empty and clean ultrasonic bath. That is, with no DES present. The particular ultrasonic bath used for this experiment is sold under the trademark OMEGASONICS QUANTUM SERIES MODEL 7400. After 60 seconds, 1 ml of DES was placed in the ultrasonic bath directly below the sample nozzle of the LCD 3.2E. As illustrated by the data of FIG. 6, nothing beyond the normal noise-level reading was recorded during the time period when the DES was added at 60 seconds and up until 120 seconds. That is, even though the DES was added to the sample matrix directly below the sample nozzle of the LCD 3.2E, there was no response created in the detector output. At the 120-second mark, ultrasonic agitation of the bath was initiated. At approximately the 190-second mark, the LCD 3.2E showed a response characteristic of a positive agent identification. The signal continued to increase with a peak near the 300-second mark and a strong signal continuing until the LCD 3.2E was turned off at approximately the 375-second mark.

In addition to the ultrasonic mechanical agitation, which as illustrated in FIG. 6 can improve detection capability, the present invention provides for a heated solvent gas to be delivered to the sample matrix, thereby heating the sample matrix. The sampled gas is heated as well. Given the increase in vapor pressure with an increase in temperature, this improves detection capability, especially for the low volatility agents such as VX. The solvent or inlet gas used with the present invention may be air, nitrogen, fluorocarbons, chlorofluorocarbon, haloalkanes, or any other suitable gas. While not required, solvents with high vapor phase solubility with the low-volatility hazards of interest would be beneficial.

While specific embodiments of the invention have been described, it will be understood that additional embodiments and various modifications may be made without departing from the spirit and scope of the invention. For example, various sonicators can be used as a component of the present invention. Various probes and probe tip shapes can be used. The inlet and outlet conduits need not have circular cross-sections and could be parallel instead of concentric. Also, the device of the present invention may be used with various detection means, including handheld detectors, laboratory-type instruments, or sample storage vessels for subsequent analysis. Accordingly, these and other embodiments of the invention fall within the scope of the following claims.

What is claimed is:

1. A device for use with a detection means and a solvent source for sampling low volatility hazardous chemicals within a sample matrix, comprising:
    a sonicator having a probe for providing mechanical agitation to the sample matrix;
    means for transporting solvent gas from the solvent source to the sample matrix;
    means for transporting sample gas from the sample matrix to the detection means; and
    a heating element for heating the sample gas, solvent gas, and sample matrix.

2. The device as recited in claim 1, wherein:
    said means for transporting solvent gas from the solvent source to the sample matrix comprises a first manifold having an inlet port and an inlet conduit confluent with said inlet port for transporting solvent gas from the solvent source to the sample matrix, said first manifold having a housing for holding said sonicator;
    said means for transporting sample gas from the sample matrix to the detection means comprises a second manifold mounted to said first manifold having an outlet port and an outlet conduit confluent with said outlet port for transporting sample gas from the sample matrix to the detection means; and
    said heating element for heating the sample gas, solvent gas, and sample matrix is attached to the outlet conduit.

3. The device as recited in claim 2, wherein said second manifold is mounted to said first manifold with said inlet conduit substantially disposed within said outlet conduit.

4. The device as recited in claim 2, further comprising a thermocouple attached to said second manifold for providing a temperature reading.

5. The device as recited in claim 2, wherein said first manifold and said second manifold are made of stainless steel.

6. The device as recited in claim 2, wherein said sonicator is fixable within said housing with said probe substantially disposed within said inlet conduit.

7. The device as recited in claim 6, further comprising a compression fitting for mounting said sonicator within said housing.

8. The device as recited in claim 6, further comprising a threaded fitting for mounting said sonicator within said housing.

9. The device as recited in claim 6, further comprising a bayonet-type fitting for mounting said sonicator within said housing.

10. The device as recited in claim 2, wherein said sonicator is a handheld device with a metal probe.

11. The device as recited in claim 10, wherein said metal probe has a plurality of interchangeable probe tips of different shapes.

12. The device as recited in claim 10, wherein said metal probe has a tip energy in the range of 100 to 150 Watts/cm$^2$.

13. The device as recited in claim 10, wherein said metal probe has a variable stroke speed and a stroke distance between 80 and 100 microns.

14. The device as recited in claim 10, wherein said metal probe is approximately ⅛-inch in diameter and approximately six inches in length.

15. The device as recited in claim 10, wherein said metal probe is made of titanium.

16. The device as recited in claim 10, wherein said metal probe is made of stainless steel.

\* \* \* \* \*